US00PP19233P2

(12) United States Plant Patent
Lyrene

(10) Patent No.: US PP19,233 P2
(45) Date of Patent: Sep. 16, 2008

(54) SOUTHERN HIGHBUSH BLUEBERRY PLANT NAMED 'SCINTILLA'

(50) Latin Name: *Vaccinium corymbosum L.*
Varietal Denomination: Scintilla

(75) Inventor: Paul M. Lyrene, Micanopy, FL (US)

(73) Assignee: The University of Florida Board of Trustees, Gainesville, FL (US)

( * ) Notice: Subject to any disclaimer, the term of this patent is extended or adjusted under 35 U.S.C. 154(b) by 0 days.

(21) Appl. No.: 11/973,429

(22) Filed: Oct. 9, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Jondle & Associates, P.C.

(57) ABSTRACT

A southern highbush blueberry (*Vaccinium corymbosum*) cultivar particularly distinguished by having a chilling requirement of 200 to 300 hours below 7° C., a vigorous bush with good survival in the field and producing early-ripening berries that are large, sweet, and firm with a powdery blue surface on the ripe berries, with good scars, firmness and flavor and berries that are borne in loose clusters, is disclosed.

4 Drawing Sheets

Genus and species: *Vaccinium corymbosum* L.
Variety denomination: 'Scintilla'.

BACKGROUND OF THE NEW PLANT

The invention relates to a new and distinct variety of southern highbush blueberry (*Vaccinium corymbosum* L) hybrid named 'Scintilla'. 'Scintilla' is a southern highbush blueberry clone which is intended for use in production of early-season, fresh-market blueberries. 'Scintilla' is distinguished by its low chilling requirement, its vigorous, disease-resistant bush, and by its large, sweet berries that ripen from mid-April through mid-May when grown in north Florida. Several thousand plants of 'Scintilla' have been propagated by softwood cuttings at Gainesville, Fla. and the resulting plants have all been phenotypically indistinguishable from the original plant.

'Scintilla' originated as a seedling from the cross between the proprietary female parent 'FL 96-43' (unpatented) with the proprietary male parent 'FL 96-26' (unpatented) made as a part of the University of Florida breeding program in a greenhouse at Gainesville, Fla. in February 1997. The seedling was first fruited in a high-density field nursery in the spring of 1999. After the second fruiting, which was observed in the field in the spring of 2000, 'Scintilla' was propagated by softwood cuttings in June, 2000 and a 20-plant plot was established in a test plot in a commercial field at Windsor, Fla. in January 2001. In June, 2002, the clone was again propagated by softwood cuttings to establish test plantings at 4 locations in north and central Florida (Windsor, Waldo, Archer and Lake Hamilton), with the total number of plants exceeding 1,000. These plants have been evaluated annually during fruiting season and at various other times throughout the year. The present invention has been found to retain its distinctive characteristics through successive asexual propagations.

SUMMARY OF THE INVENTION

The following are the most outstanding and distinguishing characteristics of this new cultivar when grown under normal horticultural practices in Florida.

1. A very low chilling requirement;
2. High vigor and early leafing in the spring;
3. Early ripening (50% ripe berries in north Florida ripen by April 27, about the same as for 'Star'); and
4. Berries that are large, sweet, and firm with a powdery blue surface on the ripe berries.

DESCRIPTION OF THE PHOTOGRAPHS

The color chart used in this specification is "The Pantone Book of Color", by Leatrice Eiseman and Lawrence Herbert. (1990). Harry N. Abrams, Inc., Publishers, N.Y. Where colors in the photographs differ from the Pantone color designations in the descriptions, the Pantone color designations are accurate. The colors shown are as true as can be reasonably obtained by conventional photographic procedures.

FIG. 1 shows a row of 'Scintilla' plants in late April in north Florida. These plants are 4 and one-half-years-old and the plot was started with small, rooted cuttings. The large berries and semi-upright growth habit are shown.

DESCRIPTION OF THE NEW CULTIVAR

Figure 1:
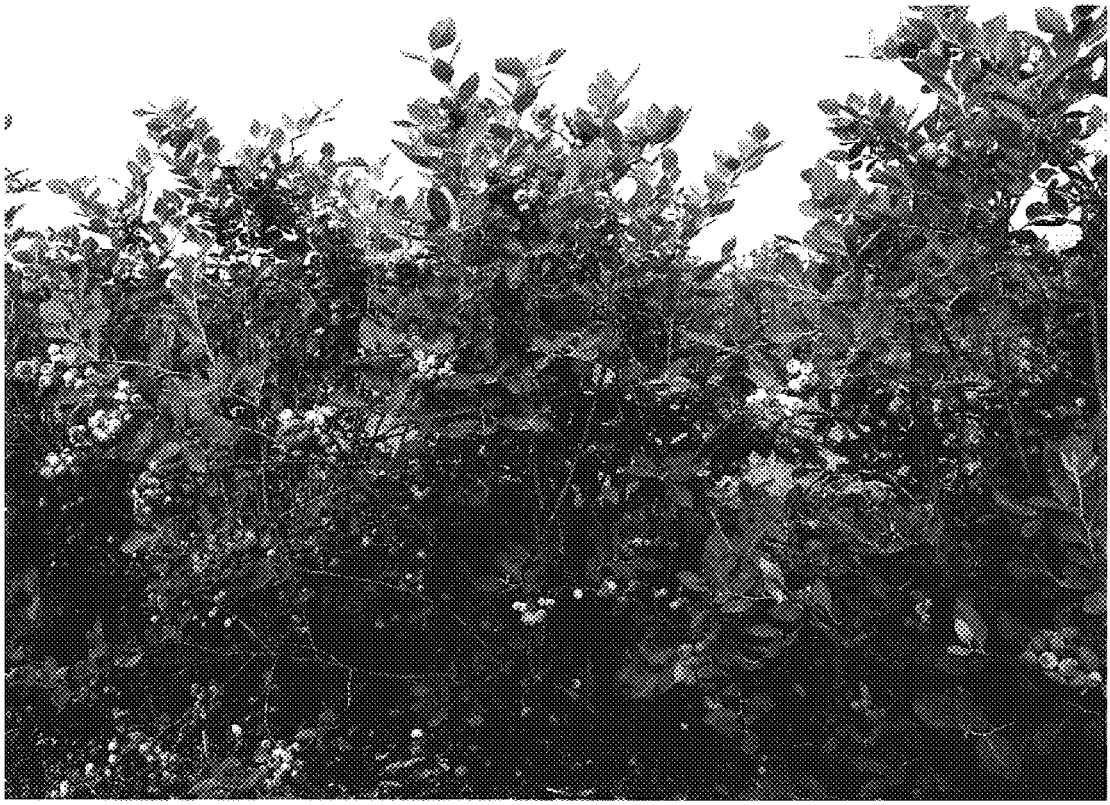
Figure 2:
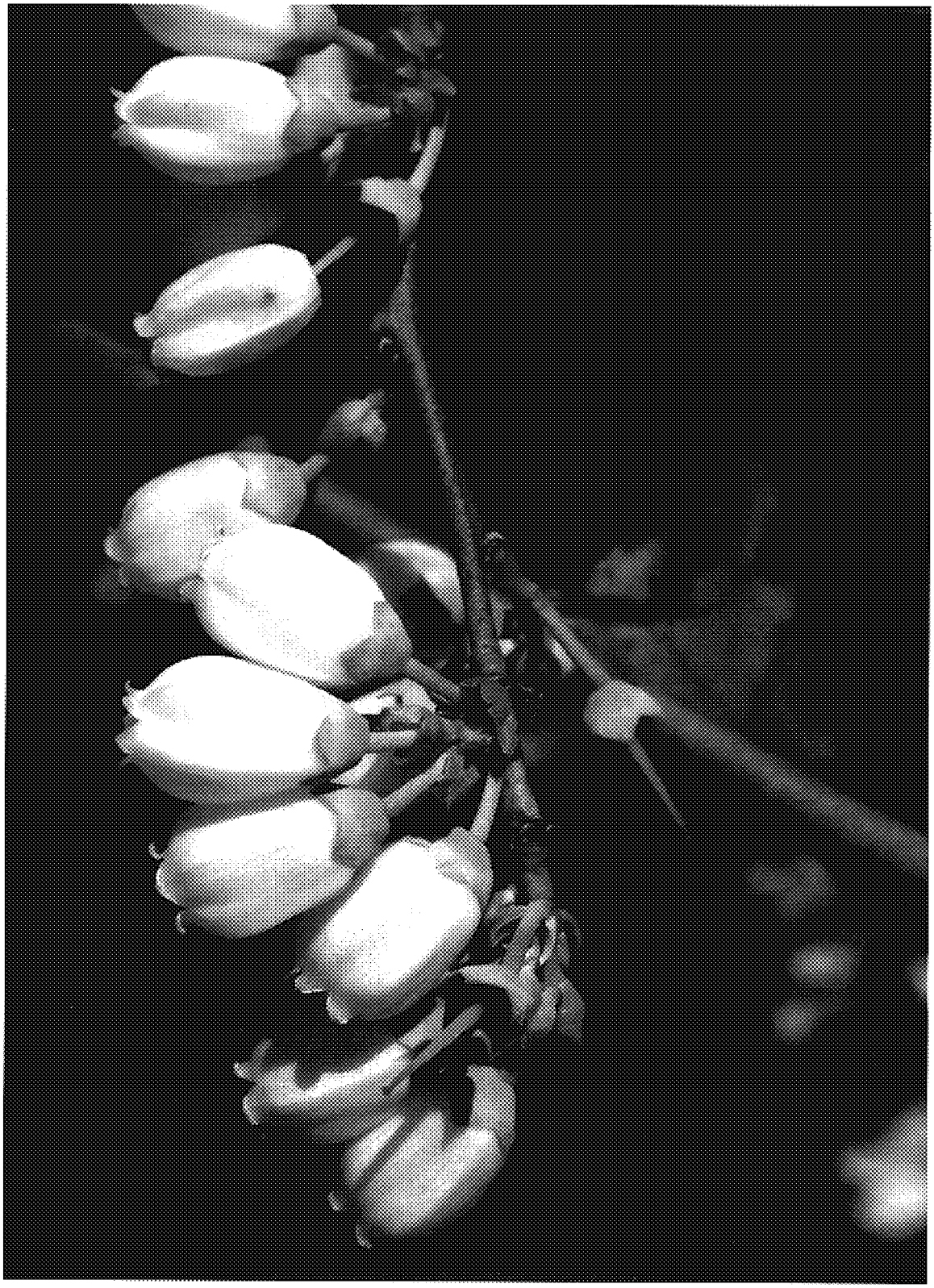
FIG. 2 shows several clusters of flowers in the field in early February, some of which have been pollinated and have shed the corolla.
Figure 3:
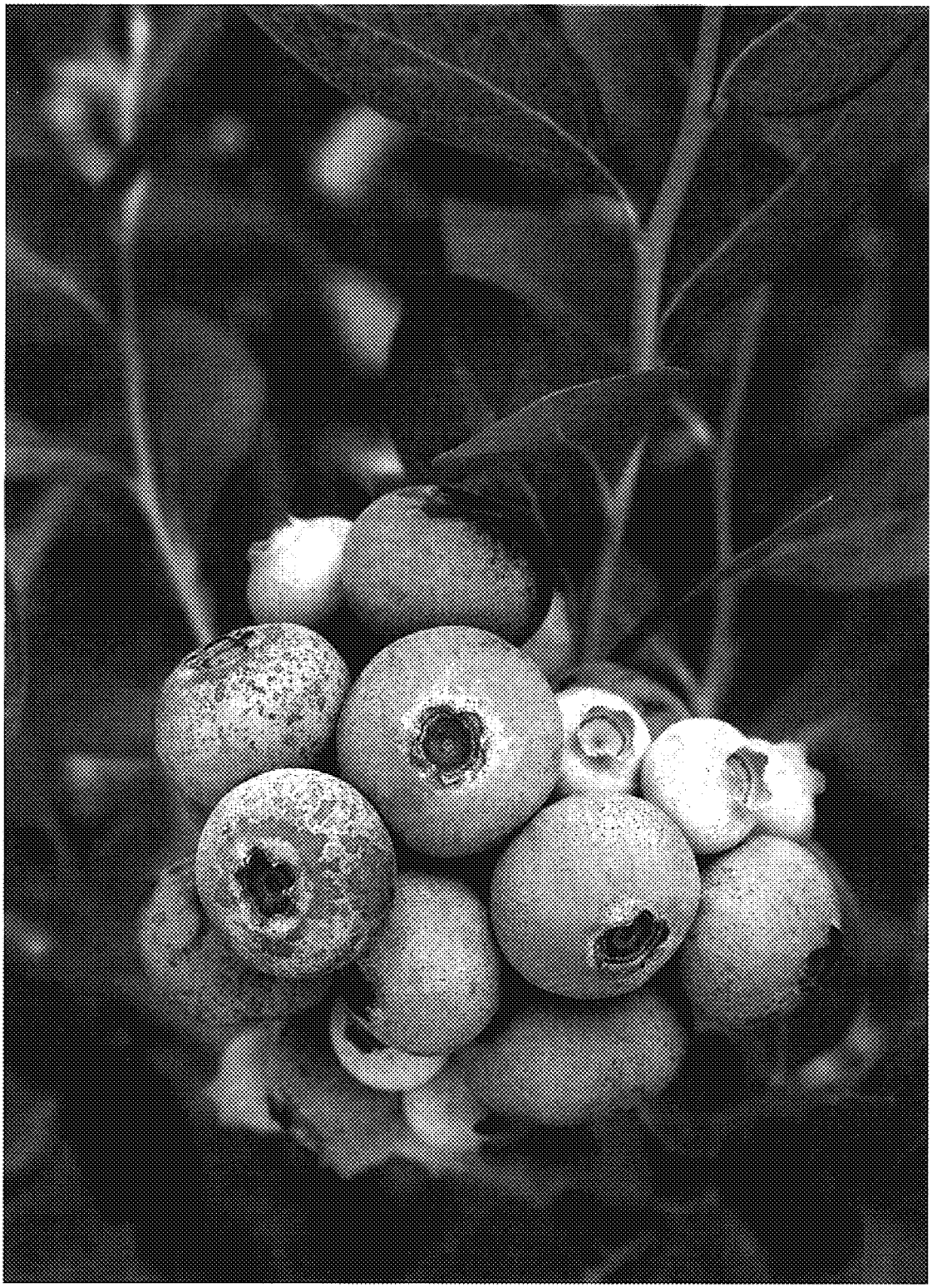
FIG. 3 shows clusters containing mature and immature berries on a field-grown plant. The freckling is due to overhead irrigation with water that is naturally high in minerals and is not an inherent feature of the berry.
Figure 4:
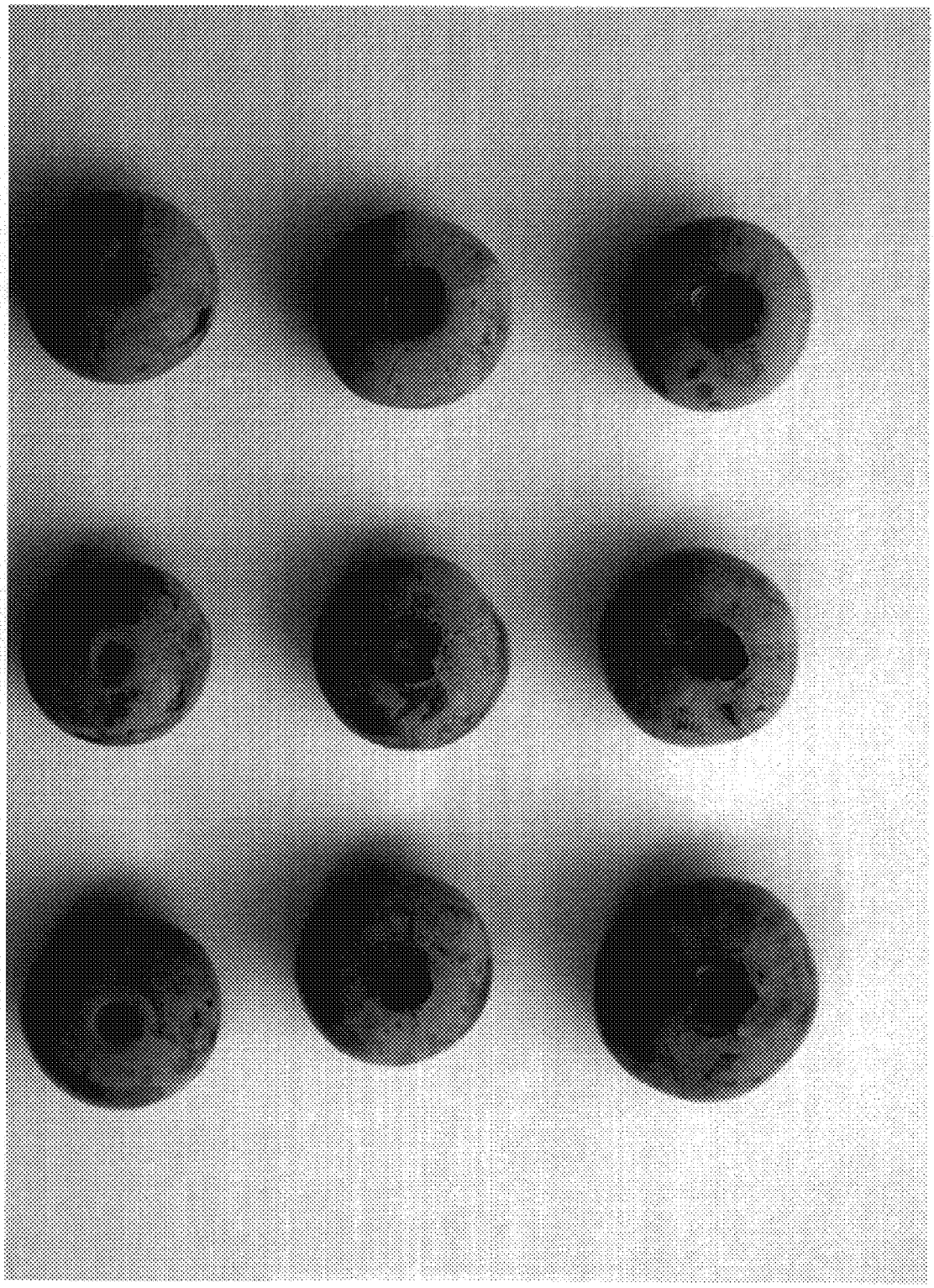
FIG. 4 shows berries at a close range. The small, dry picking scar and relatively undeveloped calyx lobes are visible.

The following detailed description sets forth the distinctive characteristics of 'Scintilla'. The data which define these characteristics were collected from asexual reproductions carried out in Florida. The plant history was taken on 4-and one-half year-old plants. The following descriptions relate to plants grown in a field in north Florida (Windsor, Fla.).

Color designations are from "The Pantone Book of Color" by Leatrice Eiseman and Lawrence Herbert; Harry N. Abrams, Inc., Publishers, New York (1990). Where the Pantone color designations differ from the colors in the photographs, the Pantone colors are accurate.

DETAILED BOTANICAL DESCRIPTION

Classification:

*Family.*—Ericaceae.

*Botanical.*—*Vaccinium corymbosum* L.

*Common name.*—Southern Highbush Blueberry.

Parentage:

*Female parent.*—'FL 96-43', a proprietary southern highbush blueberry plant (unpatented).

*Male parent.*—'FL 96-26', a proprietary southern highbush blueberry plant (unpatented).

Market class: 'Scintilla' produces southern highbush blueberries suitable for both the fresh and processed fruit markets.

Plant:

*General.*—Bush characteristics were taken from a plot of twenty 4 and one-half-year-old plants growing in a test plot in a commercial field near Windsor in northeast Florida.

*Plant height.*—2.2 m.

*Canopy* (*diameter measured at widest part of the bush*).—2.8 m.

*Plant vigor.*—High; more vigorous than 'Star'.

*Growth habit.*—Between upright and spreading.

*Flower bud density* (*number*) *along flowering twigs in January.*—Medium.

*Twigginess.*—Medium.

*Tendency toward evergreenness.*—Medium.

*Productivity and precocity.*—In northeast Florida, 'Scintilla' produces about 5 pounds of berries per bush on plants 3 years old or older. The plants will produce a small crop in their first year, but the first economically-important crop is produced in the second year.

*Chilling requirement.*—200 to 300 hours below 7° C.

*Cold hardiness.*—Flowers and fruit are hardy to −3° C.; during winter dormancy, the plant is hardy to −15° C.

*Ease of propagation.*—'Scintilla' is easy to propagate from softwood cuttings. The plants survive and grow well in nursery beds.

Trunk and branches:

*Suckering tendency.*—Medium; four-year-old plants have an average of 10 major canes rising from a crown 30 cm in diameter.

*Surface texture* (*of strong 1-year-old shoots observed in mid-December*).—Smooth.

*Surface texture* (*of strong, 1-year-old wood observed in August*).—Becoming rough due to vertical fissures filled with rough, corky bark

*Surface texture* (*of 3-year-old and older wood*).—Rough, with fine-textured, vertical cracks.

*Color of 6-month-old twigs observed in August in the field.*—"Sweet Pea", Pantone 15-0531.

*Color of 1-year-old, rough bark observed in August.*—Becoming "Brown Stone", Pantone 19-1322.

*Color of 3-year-old rough-textured canes.*—"Cement", Pantone 14-0708.

*Internode length on strong, upright shoots measured on February 1.*—Average is 1.6 cm.

Leaves:

*Length, median* (*including petiole, from tip of petiole to end of blade*).—5.9 cm.

*Width, median* (*at widest point*).—2.8 cm.

*Shape.*—Ovate; terminating in a short dew tip, 0.3 mm long which is visible with a 15× microscope.

*Margin.*—Entire; slightly revolute along the margin of the petiolar half of the blade.

*Color.*—Upper surface: "Periodot", Pantone 17-0336. Lower surface: "Tarragon", Pantone 15-0326.

*Pubescence.*—Upper surface: Glabrous but with numerous very short, white hairs visible at 30× magnification along the midrib. Lower surface: Absent.

*Pubescence on margins.*—Absent.

*Relative time of leafing versus flowering.*—In commercial fields in North Florida where 'Scintilla' is sprayed with hydrogen cyanomide in midwinter, 'Scintilla' produces new leaves starting at the time of flowering.

Flowers:

*Arrangement.*—Flowers arranged alternately along a short, leafless, deciduous branch.

*Fragrance.*—Little or none.

*Shape.*—Urceolate to cylindrical.

*Flowering period.*—Mean date of 50% open flower in Windsor, Fla. is January 27; average is 15 days before 'Star'.

*Cluster* (*tight, medium, loose*).—Loose.

*Average number of flowers per cluster.*—6.

*Petals.*—Fused into a corolla with 5 lobes.

*Pedicel.*—Length at time of anthesis: Median is 0.7 cm. Color: "Cashmere Rose", Pantone 16-2215.

*Peduncle.*—Length at time of anthesis: Highly variable; median is 0.6 cm. Color: "Claret Red", Pantone 17-1740.

*Calyx.*—Cup diameter at anthesis (tip of lobe to tip of opposite lobe): 0.5 cm; calyx lobes are unusually short for a southern highbush blueberry cultivar. Surface texture: Smooth. Color at anthesis: "Spray", Pantone 13-6007.

*Corolla.*—Length of tube: 0.9 cm to 1.0 cm. Diameter of tube (at widest point): 0.8 cm. Aperture diameter: 0.3 cm to 0.4 cm. Surface texture: Smooth. Color at anthesis: Closest to but whiter than "Turtledove", Pantone 12-5205. Length (from pedicel attachment point to corolla tip excluding the pedicel): 1.1 cm to 1.2 cm.

Reproductive organs:

*Style length* (*top of ovary to stigma tip*).—0.9 cm.

*Style color at anthesis.*—"Mellow Green", Pantone 12-0426.

*Location of tip of stigma relative to lip of the corolla.*—Stigma tip is about 0.2 cm inside of the end of the corolla tube; if the style were 0.2 mm longer, the stigma tip would extend just to the outer edge of the corolla tube.

*Pollen.*—General: The pollen includes some tetrads in which one or two spores have aborted. Although pollen staining appears to be slightly below normal, pollen fertility is not expected to be a problem in commercial fields. The clone is highly fertile, both as a male and female, in crosses in the greenhouse. Abundance of shed: High. Staining with 2% acetocarmine (a measure of potential pollen fertility): 98%. Color of dried pollen: "White Swan", Pantone 12-0000.

Self fruitfulness: Not highly self-fruitful; requires cross pollination with other southern highbush cultivars to achieve full fruit set.

Fruit:

*Mean date of first commercial harvest* (*in northeast Florida* (*Windsor*) *and 25% of berries ripe*).—April 20.

*Mean date of mid-harvest.*—Averages about April 28 which is about 1 day earlier than 'Star'.

*Mean date of last harvest.*—May 15.

*Diameter of calyx aperture on mature berry.*—0.7 cm.

*Size and shape of calyx lobes on mature berry.*—Lobes small and inconspicuous; calyx lobes are irregularly-shaped.

*Depth of calyx dish.*—0.2 cm.

*Pedicel length on ripe berry.*—Median is 0.6 cm.

*Peduncle length on ripe berry.*—Variable; typically about 0.5 cm to 0.8 cm.

*Detachment force for ripe berries.*—Medium to low.

*Number of berries per cluster.*—Median is 5.

Berry:

*Cluster* (*tight, medium, or loose*).—Loose.

*Weight* (*on well-pruned plants*).—2.5 g per berry compared to 1.8 g per berry for 'Star'.

*Height.*—1.26 cm.

*Width.*—1.76 cm.

*Shape.*—Subglobose; the polar diameter is shorter than the equatorial diameter.

*Surface color of mature berries while on the plant.*—"Lilac Gray", Pantone 14-3903.

*Surface color of the berries after harvesting and packing.*—"Neutral Gray", Pantone 17-4402.

*Surface color of ripe berry after polishing.*—"Shale", Pantone 19-3903.

*Internal flesh color of ripe berry.*—"Lint", Pantone 14-0216.

*Surface wax.*—Medium in amount and in persistence.

*Pedicel scar.*—Small and dry.

*Firmness.*—High.

*Flavor.*—Sweet with medium acidity.

*Texture.*—Good; small seeds, very juicy and thin-skinned.

Seeds:

*Color of dried seeds.*—"Brown Sugar", Pantone 17-1134.

*Weight of well-developed dried seed.*—0.565 mg per seed.

*Length of well-developed dried seed.*—Mean is 0.25 cm.

*Width of well-developed dried seed.*—Mean is 0.095 cm.

Resistance to diseases, insects and mites: 'Scintilla' has grown vigorously and shows good bush survival in the field. 'Scintilla' appears to have above-average resistance to root rot (*Phytophthora cinnamomi*) and stem blight (*Botryosphaeria dothidia*). The plants have shown no signs of cane canker (*Botryosphaeria corticis*) susceptibility in the field. The fungal leaf spots that are common on highbush blueberries grown in Florida are easily controlled by approved fungicides.

COMPARISON WITH PARENTAL AND KNOWN CULTIVARS

'Scintilla' differs from the proprietary female (seed) parent 'FL 96-43', in that 'Scintilla' sheds pollen readily, while 'FL 96-43' sheds very little pollen. Additionally, 'Scintilla' also has a somewhat larger and sweeter berry than 'FL 96-43'.

'Scintilla' differs from the male (pollen) parent 'FL 96-26' in that 'Scintilla' has a berry that is larger and lighter in color than 'FL 96-26'.

'Scintilla' differs from the commercial variety 'Star' (U.S. Plant Pat. No. 10,675) in that 'Scintilla' is larger and more vigorous, has a lower chilling requirement and a higher resistance to the pathogenic fungus, *Botryosphaeria corticis,* which causes blueberry stem canker disease, than 'Star'. Additionally, 'Scintilla' has berries that have a much lighter bloom on the surface than 'Star'.

I claim:

1. A new and distinct cultivar of southern highbush blueberry plant as shown and described herein.

* * * * *